US010772900B2

(12) United States Patent
Beiting et al.

(10) Patent No.: US 10,772,900 B2
(45) Date of Patent: Sep. 15, 2020

(54) DRUG TARGET FOR TREATING VETERINARY INFECTIONS AND METHODS OF USING SAME

(71) Applicant: THE TRUSTEES OF THE UNIVERSITY OF PENNSYLVANIA, Philadelphia, PA (US)

(72) Inventors: Daniel P. Beiting, Moorestown, NJ (US); Ana M. Misic, Philadelphia, PA (US); Shelly C. Rankin, Philadelphia, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/318,769

(22) PCT Filed: Jul. 21, 2017

(86) PCT No.: PCT/US2017/043278
§ 371 (c)(1),
(2) Date: Jan. 18, 2019

(87) PCT Pub. No.: WO2018/022451
PCT Pub. Date: Feb. 1, 2018

(65) Prior Publication Data
US 2019/0282592 A1     Sep. 19, 2019

Related U.S. Application Data
(60) Provisional application No. 62/367,405, filed on Jul. 27, 2016.

(51) Int. Cl.
| | | |
|---|---|---|
| A61K 31/662 | (2006.01) | |
| A61P 31/04 | (2006.01) | |
| A61K 45/06 | (2006.01) | |
| C07F 9/38 | (2006.01) | |
| C07F 9/22 | (2006.01) | |
| C07F 9/6587 | (2006.01) | |
| C07F 9/46 | (2006.01) | |

(52) U.S. Cl.
CPC ............ *A61K 31/662* (2013.01); *A61K 45/06* (2013.01); *A61P 31/04* (2018.01); *C07F 9/22* (2013.01); *C07F 9/38* (2013.01); *C07F 9/46* (2013.01); *C07F 9/6587* (2013.01)

(58) Field of Classification Search
CPC . C07F 9/38; C07F 9/46; A61K 31/662; A61K 45/06; A61P 31/04; A01N 57/10
See application file for complete search history.

(56) References Cited

U.S. PATENT DOCUMENTS

| | | |
|---|---|---|
| 5,169,645 A | 12/1992 | Shukla et al. |
| 6,323,219 B1 | 11/2001 | Costanzo |
| 2001/0046976 A1 | 11/2001 | Class et al. |
| 2015/0164926 A1* | 6/2015 | Froyman ............... A61P 31/12 514/23 |
| 2017/0216252 A1* | 8/2017 | Young .................. C07D 209/12 |

OTHER PUBLICATIONS

Uh (Bioorganic and Medicinal Chemistry Letters vol. 21 pp. 6973-6976 published 2011) (Year: 2011).*
International Search Report and Written Opinion for PCT International Application No. PCT/US2017/043278 dated Oct. 16, 2017.
Beach , et al., "Nucleotide Sequence and Expression in *Escherichia coli* of the 3-hydroxy-3-methylglutaryl Coenzyme A Lyase Gene of Pseudomonas Mevalonii", J Bacteriol. 171(12), Dec. 1989, 6468-6472.
Begley , et al., "Analysis of the Isoprenoid Biosynthesis Pathways in Listeria Monocytogenes Reveals a Role for the Alternative 2-C-methyl-D-erythritol 4-phosphate Pathway in Murine Infection", Infect Immun. 76(11), Nov. 2008, 5392-5401.
Borrmann , et al., "Fosmidomycin-clindamycin for the Treatment of Plasmodium Falciparum Malaria", J Infect Dis. 190(9), Nov. 2004, 1534-1540.
Boucher , et al., "The Role of Lateral Gene Transfer in the Evolution of Isoprenoid Biosynthesis Pathways", Mol Microbiol. 37(4), Aug. 2000, 703-716.
Deinhofer , et al., "*Staphylococcus* spp. as mastitis-related pathogens in goat milk", Vet Microbiol. Feb. 1995;43(2-3), Feb. 1995, 161-166.
Heuston , et al., "Isoprenoid Biosynthesis in Bacterial Pathogens", Microbiology 158(Pt 6), Jun. 2012, 1389-1401.
Jindal , et al., "*Staphylococcus schleiferi* Meningitis in a Child", Pediatr Infect Dis J. 34(3), Mar. 2015, 329.
Kuan , et al., "Canine *Staphylococcus pseudintermedius* Sinonasal Infection in Human Hosts", Int Forum Allergy Rhinol. 6(7), Jul. 2016, 710-715 (abstract only).
Kuzuyama , "Mevalonate and nonmevalonate pathways for the biosynthesis of isoprene units", Biosci Biotechnol Biochem. Aug. 2002;66(8), Aug. 2002, 1619-1627.
Lange , et al., "Isoprenoid Biosynthesis: The Evolution of Two Ancient and Distinct Pathways Across Genomes", Proc Natl Acad Sci U S A. 97(24), Nov. 2000, 13172-13177.
Lowy , et al., "*Staphylococcus aureus* Infections", N Engl J Med. 339(8), Aug. 1998, 520-532 (abstract only).
Misic , et al., "Complete Genome Sequence and Methylome of *Staphylococcus schleifer*, an Important Cause of Skin and Ear Infections in Veterinary Medicine", Genome Announc. 3(5), Sep. 2015, e01011-e01015.
Misic , et al., "Divergent Isoprenoid Biosynthesis Pathways in Staphylococcus Species Constitute a Drug Target for Treating Infections in Companion Animals", mSphere. 1(5), Sep. 2016, e00258-16.

(Continued)

*Primary Examiner* — Timothy P Thomas
*Assistant Examiner* — George W Kosturko
(74) *Attorney, Agent, or Firm* — Saul Ewing Arnstein & Lehr, LLP; Kathryn Doyle; Jacque Young

(57) ABSTRACT

The invention includes a method of treating or preventing a *Staphylococcus* infection in a mammal or avian species in need thereof. The methods comprise administering to the mammal or avian species a therapeutically effective amount of fosmidomycin. In certain embodiments, the methods treat or prevent a drug-resistant *Staphylocoocccus* infection.

21 Claims, 8 Drawing Sheets

(56) References Cited

OTHER PUBLICATIONS

Missinou, et al., "Fosmidomycin for Malaria", Lancet. 360(9349), Dec. 2002, 1941-1942 (abstract only).

Na-Bangchang, et al., "Pharmacokinetics and pharmacodynamics of fosmidomycin monotherapy and combination therapy with clindamycin in the treatment of multidrug resistant falciparum malaria", Malar J. 6, May 2007, 70.

Odom, et al., "Five Questions About Non-Mevalonate Isoprenoid Biosynthesis", PLoS Pathog. 7(12), Dec. 2011, e1002323.

Powers, et al., "Igniting the Fire: *Staphylococcus aureus* Virulence Factors in the Pathogenesis of Sepsis", PLoS Pathog. 10(2), Feb. 2014, e1003871.

Poyart, et al., "Rapid and Accurate Species-Level Identification of Coagulase-Negative Staphylococci by Using the sodA Gene as a Target", J Clin Microbiol. 39(12), Dec. 2001, 4296-4301.

Scher, et al., "3-Hydroxy-3-methylglutaryl Coenzyme A Lyase From Pseudomonas Mevalonii", iochim Biophys Acta. 1003(3), Jun. 1989, 321-326 (abstract only).

Schlievert, et al., "Role of Superantigens in Human Disease", J Infect Dis. 167(5), May 1993, 997-1002 (abstract only).

Steinbacher, et al., "Structural Basis of Fosmidomycin Action Revealed by the Complex With 2-C-methyl-D-erythritol 4-phosphate Synthase (IspC). Implications for the Catalytic Mechanism and Anti-Malaria Drug Development", J Biol Chem. 278(20), May 2003, 18401-18407.

Szweda, et al., "Antibiotic resistance in Staphylococcus aureus strains isolated from cows with mastitis in eastern Poland and analysis of susceptibility of resistant strains to alternative nonantibiotic agents: lysostaphin, nisin and polymyxin B", J Vet Med Sci. 76(3), Nov. 2013, 355-362.

Takagi, et al., "A gene cluster for the mevalonate pathway from *Streptomyces* sp. Strain CL190", J Bacteriol. 182(15), Aug. 2000, 4153-4157.

Ververidis, et al., "Experimental staphylococcal mastitis in bitches: clinical, bacteriological, cytological, haematological and pathological features", Vet Microbiol. 124(1-2), Sep. 2007, 95-106.

Wilding, et al., "Identification, Evolution, and Essentiality of the Mevalonate Pathway for Isopentenyl Diphosphate Biosynthesis in Gram-Positive Cocci", J Bacteriol. 182(15), Aug. 2000, 4319-4327.

Zhang, et al., "A Second Target of the Antimalarial and Antibacterial Agent Fosmidomycin Revealed by Cellular Metabolic Profiling", Biochemistry 50(17), May 2011, 3570-3577.

\* cited by examiner

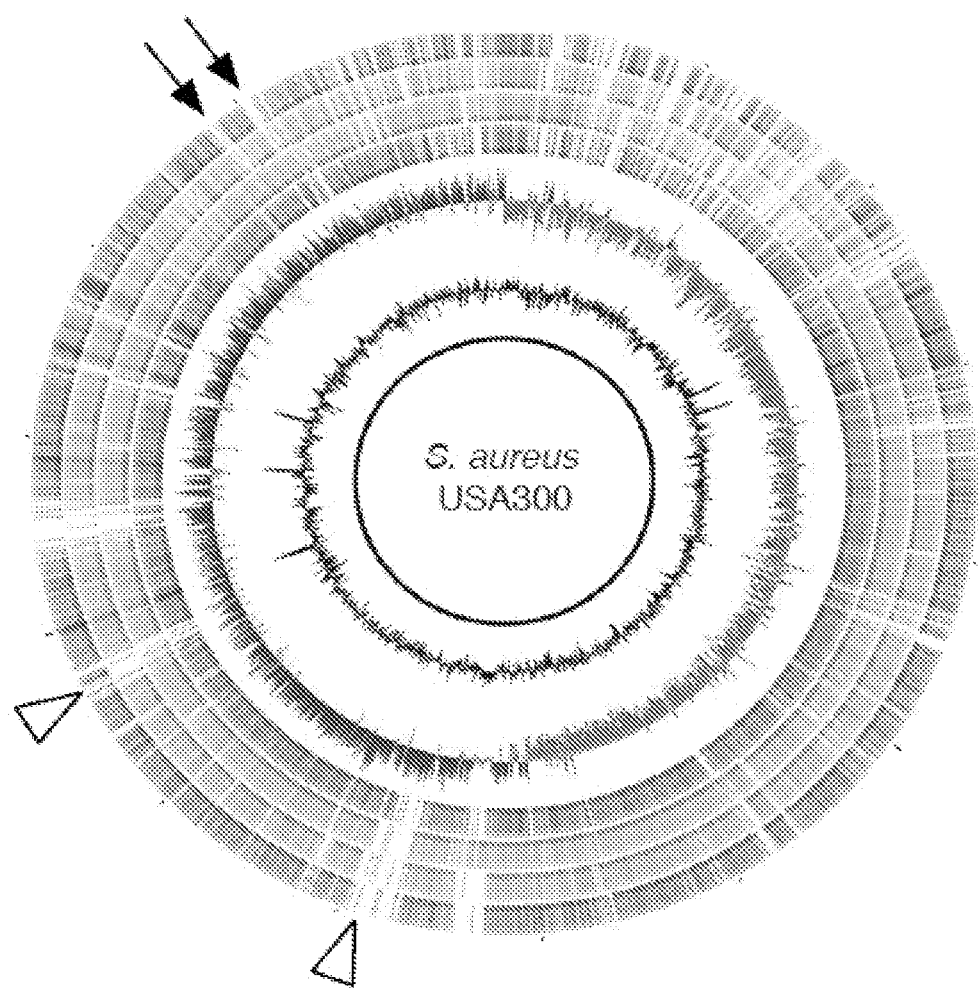
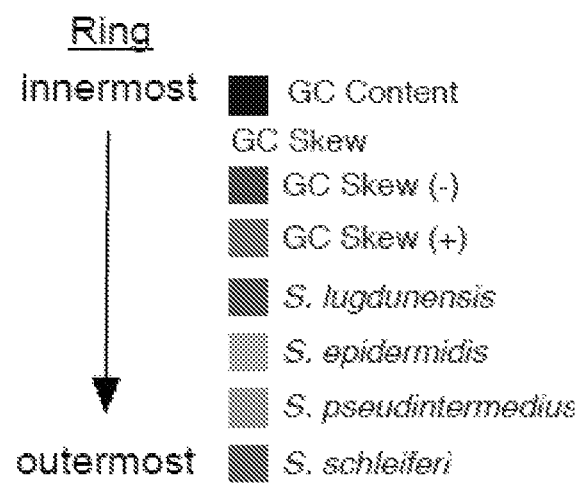
Fig. 1A

A

B

| Species (strain) | MIC (µg/mL) | MBC (µg/mL) |
|---|---|---|
| S. schleiferi (1360-13) | 1 | 16 |
| S. schleiferi (2142-05) | 1 | 4 |
| S. schleiferi (2317-03) | 0.5 | 128 |
| S. schleiferi (5909-02) | 8 | 128 |
| S. pseudintermedius (11680P) | 1 | 64 |
| S. pseudintermedius (5317) | 0.5 | 32 |
| S. sciuri (1250OP-14) | 0.5 | 64 |
| S. aureus (MRSA; 3964) | No Inhibition | No Inhibition |
| S. aureus (MSSA; 3899) | No Inhibition | No Inhibition |
| S. epidermidis (1151OP-12) | No Inhibition | No Inhibition |
| S. lugdunensis (F36680) | No Inhibition | No Inhibition |

|  | \multicolumn{4}{c}{S. schleiferi strain} |
| --- | --- | --- | --- | --- |
|  | 1360-13 | 2142-05 | 5909-02 | 2317-03 |
| Source | Skin Pyoderma | Ear (otitis) | Skin Pyoderma | Skin Pyoderma |
| Date obtained | 5/14/13 | 5/3/05 | 12/16/02 | 5/21/03 |
| Biochemical Test Results: | | | | |
| Coagulase | + | - | - | - |
| Urease | + | + | + | + |
| Oxacillin resistance | + | - | + | + |
| Beta-lactamase | + | - | + | + |
| Antimicrobial Susceptibility Results: | | | | |
| Ampicillin | R | S | R | R |
| Amoxicillin-clavulanic acid | S | S | S | S |
| Chloramphenicol | I | S | S | S |
| Clindamycin | R | S | R | S |
| Cefazolin | R | S | R | S |
| Ciprofloxacin | R | S | R | R |
| Erythromycin | R | S | R | S |
| Gentamicin | I | S | S | I |
| Imipenem | S | S | S | S |
| Oxacillin | R | S | R | R |
| Penicillin | R | S | R | R |
| Rifampin | S | S | S | S |
| Trimethoprim-sulfamethoxazole | S | S | S | S |
| Tetracycline | R | S | S | S |
| Vancomycin | S | S | S | S |

Fig. 5

A
| | S. schleiferi strain | | | |
|---|---|---|---|---|
| | 1360-13 | 2142-05 | 5909-02 | 2317-03 |
| Number of bases | 254,658,029 | 186,490,724 | 296,467,696 | 513,968,998 |
| Number of Reads | 57,563 | 45,892 | 60,630 | 87,755 |
| N50 read length | 7,069 | 6,475 | 7,782 | 10,393 |
| Mean read length | 4,423 | 4,063 | 4,889 | 5,856 |
| Mapped Reads | 50,911 | 41,462 | 53,607 | 78,156 |
| Average ref. coverage | 76.49 | 59.38 | 84.72 | 139.81 |
| Consensus accuracy (%) | 99.99 | 99.99 | 99.99 | 99.99 |
B
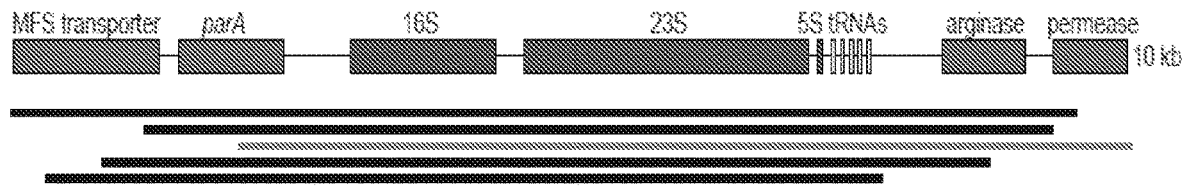
C
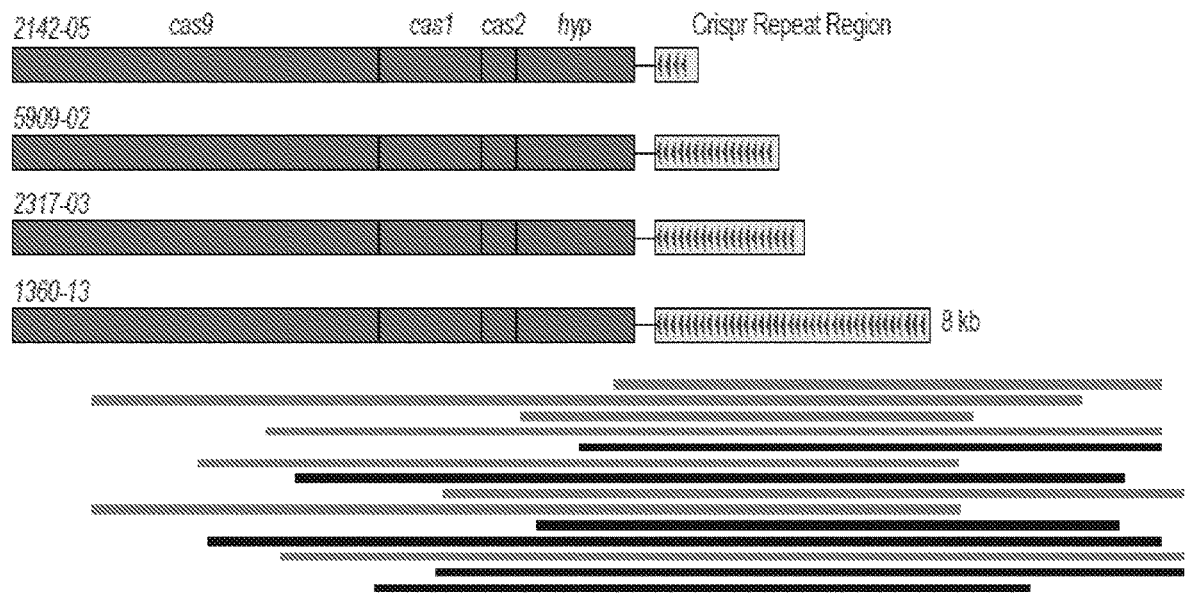
Figs. 6A-6C

DRUG TARGET FOR TREATING VETERINARY INFECTIONS AND METHODS OF USING SAME

CROSS-REFERENCE TO RELATED APPLICATIONS

The present application is a 35 U.S.C. § 371 national phase application from, and claims priority to, International Application No. PCT/US2017/043278, filed Jul. 21, 2017, and published under PCT Article 21(2) in English, which claims priority under 35 U.S.C. § 119(e) to U.S. Provisional Patent Application No. 62/367,405, filed Jul. 27, 2016, all of which applications are incorporated herein by reference in their entireties.

BACKGROUND OF THE INVENTION

*Staphylococcus* infections pose a serious health threat to humans, companion animals and livestock. *Staphylococcus aureus* is a Gram-positive bacterium that can asymptomatically colonize human skin and the anterior nares, but it is also responsible for mild to severe skin and soft tissue infections and life-threatening endocarditis, pneumonia, and sepsis. In 2011, there were approximately 80,000 invasive methicillin-resistant *S. aureus* (MRSA) infections in the United States that resulted in 11,000 deaths. Although the prevalence of MRSA carriage in companion animals is low (approximately 0-4%) and infections are rare, other *Staphylococcus* species are common commensals and pathogens in veterinary medicine. *S. schleiferi* and *S. pseudintermedius* are the leading causes of skin and ear infections in dogs; *S. hyicus* causes high-morbidity skin infections in pigs and osteomyelitis in birds, while *S. agnetis* and *S. chromogenes* cause mastitis in cattle and are associated with reduced milk quality.

The emergence of drug-resistant *Staphylococcus* is a global problem. Drugs such as erythromycin and cephalexin are commonly used to treat infections in both humans and animals, leading to concern that as resistance to shared antibiotics becomes more widespread, zoonotic transmission of either drug-resistant *Staphylococcus*, or horizontal transfer of resistance genes may render these treatments ineffective for both humans and animals. Despite this concern, there is a dearth of knowledge about how *Staphylococcus* species in veterinary medicine differ from those commonly seen in human medicine.

There is a need in the art to identify novel compounds useful in the treatment of bacterial infections, especially drug-resistant *Staphylococcus* infections. The present invention addresses this need.

SUMMARY OF THE INVENTION

As described herein, the present invention relates to compositions and methods for treating or preventing a *Staphylococcus* infection in a mammal or avian species.

One aspect of the invention includes a method of treating or preventing a *Staphylococcus* infection in a mammal or avian species, comprising administering to the mammal or avian species in need thereof a therapeutically effective amount of fosmidomycin, or a salt, solvate, tautomer, enantiomer or diastereoisomer thereof, whereby the *Staphylococcus* infection is treated or prevented in the mammal or avian species.

In another aspect, the invention includes a kit comprising fosmidomycin and instructional material for use thereof in treating or preventing a *Staphylococcus* infection in a mammal or avian species.

In yet another aspect, the invention includes a kit comprising (i) fosmidomycin and (ii) an antimicrobial agent and (iii) instructional material for use thereof in treating or preventing a *Staphylococcus* infection in a mammal or avian species.

In various embodiments of the above aspects or any other aspect of the invention delineated herein, the *Staphylococcus* infection is caused by at least one *Staphylococcus* species selected from the group consisting of *S. schleiferi, S. pseudintermedius, S. sciuri, S. hyicus*, and *S. chromogenes*. In another embodiment, the *Staphylococcus* infection is caused by *S. schleiferi*. In yet another embodiment, the *Staphylococcus* infection is caused by an antibiotic resistant *Staphylococcus*. In still another embodiment, the *Staphylococcus* infection is caused by a species of *Staphylococcus* that utilizes the non-mevalonate pathway for isoprenoid biosynthesis.

In another embodiment, the mammal or avian species is selected from the group consisting of a dog, pig, cow, horse, bird, and human. In yet another embodiment, the mammal comprises a dog. In still another embodiment, fosmidomycin is administered to the mammal or avian species as a pharmaceutical composition further comprising at least one pharmaceutically acceptable carrier. In another embodiment, the mammal or avian species is further administered at least one antibacterial agent. In yet another embodiment, the fosmidomycin and the at least one antibacterial agent are co-administered to the mammal or avian species. In still another embodiment, the fosmidomycin and the at least one antibacterial agent are co-formulated. In another embodiment, the fosmidomycin is administered to the animal by at least one administration route selected from the group consisting of otic, topical, inhalational, oral, rectal, vaginal, parenteral, transdermal, pulmonary, intranasal, buccal, ophthalmic, intrathecal, intracranial, and intravenous. In yet another embodiment, the fosmidomycin is the only antibacterial agent administered to the mammal or avian species.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1E are a series of graphs illustrating comparative genomic analysis of *Staphylococcus* genomes. FIG. 1A depicts a circular alignment of whole genome sequences for five *Staphylococcus* species. Working from the innermost ring out: *S. aureus* subspecies *aureus* USA300 (solid black ring); GC content of *S. aureus* USA300; GC skew of *S. aureus* USA300; *S. lugdunensis; S. epidermidis; S. pseudintermedius* ED99; *S. schleiferi* strain 1360-13. Arrows indicate genomic regions missing from canine-associated *Staphylococcus*. Triangles point to regions missing from all strains examined, but which were present in *S. aureus* USA300. FIG. 1B is a hierarchical clustering heatmap of differentially abundant subsystems among 14 selected *Staphylococcus* genomes. FIG. 1C shows five selected subsystems found in higher abundance in *S. aureus, S. lugdunensis*, and *S. epidermidis* than in *S. pseudintermedius* or *S. schleiferi*. FIG. 1D shows five selected subsystems found in higher abundance in *S. aureus* than in all the other species examined. FIG. 1E shows two selected subsystems found in higher abundance in companion animal-associated species (*S. schleiferi* and *S. pseudintermedius*) than in human-associated species (*S. aureus, S. epidermidis*, and *S. lugdunensis*). In FIGS. 1C-1E, only subsystems for which at least two genes were different between the compared groups are shown. The grey text in panels FIG. 1C and FIG. 1E highlights isoprenoid biosynthesis pathways.

FIG. 2A is a Mueller-Hinton agar plate containing 50 µg/mL fosmidomycin and was streaked with overnight cultures of strains *S. aureus* 3964 (USA100), *S. epidermidis* 1151PP-12, *S. pseudintermedius* 11680P, and *S. schleiferi* 1360-13. FIG. 2B is a table showing minimal inhibitory concentrations (MIC) and minimal bactericidal concentrations (MBC) for eleven *Staphylococcus* strains.

FIG. 4A shows *Staphylococcus* genomes evaluated for the presence of non-mevalonate and mevalonate pathway genes as determined by KEGG. An "X" denotes a functional annotation that is present in the selected strain. Mevalonate pathway abbreviations and Enzyme Commission numbers: HMGS (EC 2.3.3.10), HMGR (EC 1.1.1.88), MK (EC 2.7.1.36), PMK (EC 2.7.4.2), PMD (EC 4.1.1.33). Non-mevalonate pathway abbreviations: DXR (EC 2.21.7), DXS (EC 1.1.1.267), ISPD (EC 2.7.7.60), ISPE (EC 2.7.1.148), ISPF (EC 4.6.1.12), ISPG (EC 1.17.7.1 or 1.17.7.3), ISPH (EC 1.17.1.2). FIG. 4B shows the locations of the mevalonate and non-mevalonate on the staphylococcal genomes (triangles). The genomes are presented as linear chromosomes and oriented such that 0 Mbp is the origin of replication.

FIG. 5 is a table showing antimicrobial susceptibility and metadata for *S. schleiferi* strains. The *S. schleiferi* strain metadata are shown, including date of collection, body site, and antibiotic susceptibility profiles. The antibiotic susceptibilities were determined using the Microscan Walkaway 40 PC20 Gram-positive combo-panel (Dade Behring, Sacramento, USA).

FIGS. 6A-6C are a series of graphs that show long sequence reads assisted in assembling long repetitive regions. FIG. 6A shows the genome statistics as determined by PacBio SMRT Analysis. FIG. 6B shows PacBio long reads span a 5 kb rRNA operon and nearby coding regions. rRNA genes, tRNA genes, and protein-coding sequences are depicted. Black and grey lines indicate sequences that map to strain 5909-02 in the forward and reverse direction, respectively (total coverage in this region is ~90X). FIG. 6C shows alignment of the CRISPR-Cas loci. Protein coding *cas* genes, clustered regularly-interspaced short palindromic repeat (CRISPR) regions, and the 36-bp CRISPR repeat sequences are depicted. Black and grey lines indicate sequences that map across the entire CRISPR repeat-spacer region in strain 1360-13 in the forward and reverse direction, respectively (total coverage in this region is ~80X). The genomes are ordered from smallest number of repeat sequences (4; strain 2142-05) to largest (36; strain 1360-13).

DETAILED DESCRIPTION OF THE INVENTION

Figures 1B, 1C, 1D, 1E:
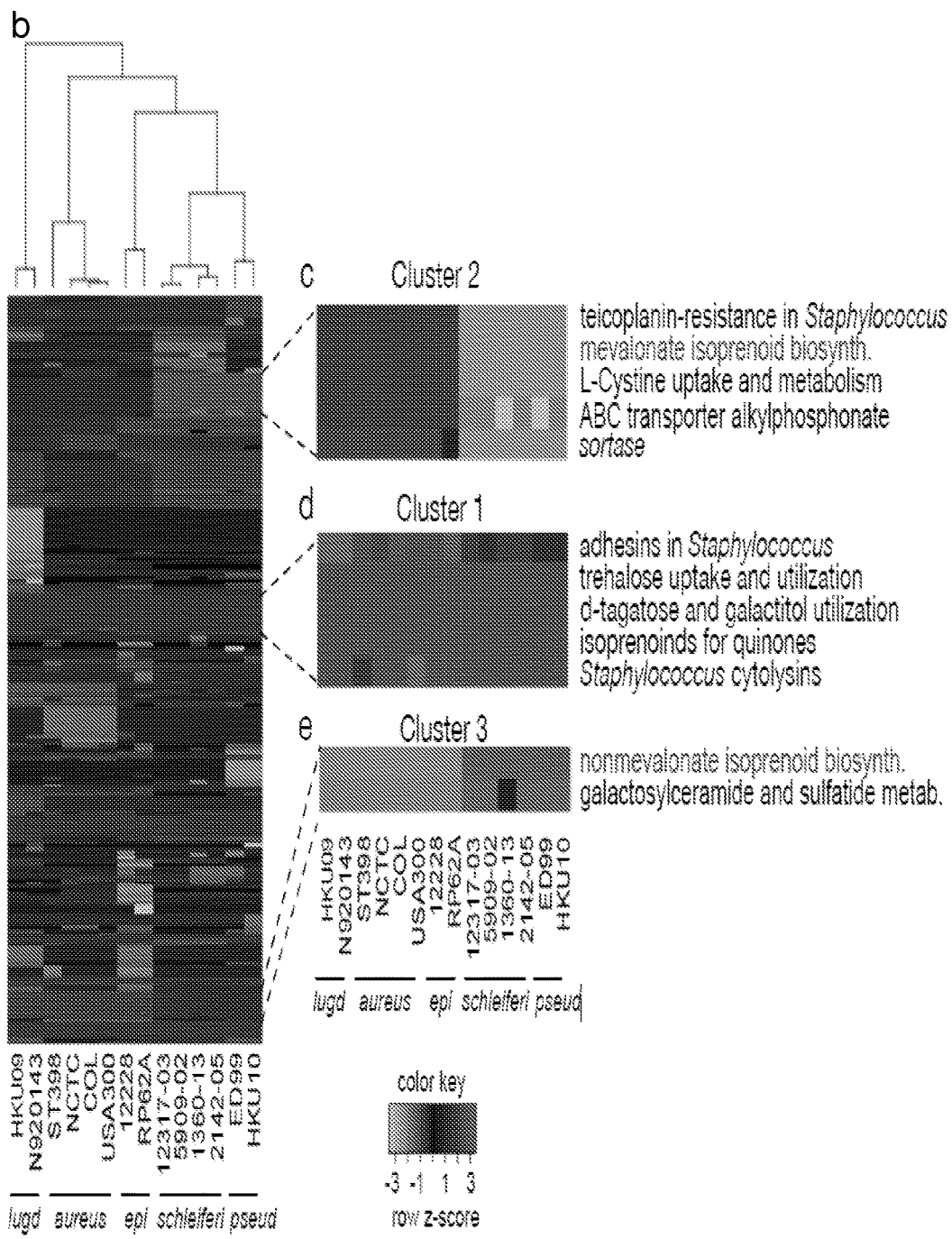

*Staphylococcus* species are a leading cause of skin and soft tissue infections in humans and animals and the antibiotics used treat these infections are often the same. Methicillin and multidrug-resistant staphylococcal infections are becoming more common in human and veterinary medicine. From a 'One-Health' perspective, this overlap in antibiotic use and resistance raises concerns over the potential spread of antibiotic resistance genes. As demonstrated herein, whole genome sequencing analysis of *Staphylococcus schleiferi*, a common cause of infections in dogs, identified the non-mevalonate pathway for isoprenoid biosynthesis. Comparative genomics analysis revealed that this pathway is conserved in veterinary-associated *Staphylococcus* species, but absent from those species typically associated with human disease. Without wishing to be bound by any specific theory, this suggests that *Staphylococcus* species use divergent pathways to synthesize isoprenoids. Those species typically associated with infection of humans and non-human primates use the mevalonate pathway, while those associated with companion animals and livestock use the non-mevalonate pathway. Although, *Staphylococcus* species typically associated with animal disease can occasionally cause infections in humans. As demonstrated herein, the antibiotic fosmidomycin, an inhibitor of the non-mevalonate pathway, was effective in killing multidrug-resistant veterinary-associated staphylococcal species but had no effect on the growth or survival of *S. aureus* and *S. epidermidis*. These data herein identify an essential metabolic pathway in *Staphylococcus* that differs between typical human- and veterinary-associated species, and demonstrates that drugs such as fosmidomycin, which target enzymes in the non-mevalonate pathway, are an effective treatment for certain staphylococcal infections.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, microbiology, pharmacology and organic chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

In one aspect, the terms "co-administered" and "co-administration" as relating to a subject refer to administering to the subject a compound of the invention or salt thereof along with a compound that may also treat diseases and/or disorders contemplated herein. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing bacterial infection in a patient.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Parenteral" administration of an immunogenic composition includes, e.g., subcutaneous (s.c.), intravenous (i.v.), intramuscular (i.m.), or intrasternal injection, or infusion techniques.

As used herein, the phrase "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the phrase "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, the phrase "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the phrase "pharmaceutically acceptable salt" refers to a salt of the administered compounds prepared from pharmaceutically acceptable non-toxic acids, including inorganic acids, organic acids, solvates, hydrates, or clathrates thereof. Pharmaceutically unacceptable salts may nonetheless possess properties such as high crystallinity, which have utility in the practice of the present invention, such as for example utility in process of synthesis, purification or formulation of compounds useful within the methods of the invention. Salts may be comprised of a fraction of one, one or more than one molar equivalent of acid or base with respect to any compound of the invention. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate). Suitable pharmaceutically acceptable base addition salts of compounds of the invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the phrase "pharmaceutical composition" refers to a mixture of at least one compound useful in the methods of the invention with a pharmaceutically acceptable carrier. The pharmaceutical composition facilitates administration of the compound to a patient. Multiple techniques of administering a compound exist in the art including, but not limited to, nasal, inhalational, topical, oral, buccal, rectal, pleural, peritoneal, vaginal, intramuscular, subcutaneous, transdermal, epidural, intratracheal, otic, intraocular, intrathecal and intravenous route administration.

The term "prevent," "preventing" or "prevention" as used herein means avoiding or delaying the onset of symptoms associated with a disease or condition in a subject that has not developed such symptoms at the time the administering of an agent or compound commences. Disease, condition and disorder are used interchangeably herein.

As used herein, the term "subject", "patient," or "individual" refers to a human or a non-human mammal and any avian species. Non-human mammals include, for example, livestock and pets, such as ovine, bovine, porcine, canine, feline and murine mammals. In some embodiments the patient, subject or individual is a dog. In some embodiments the patient, subject or individual is a canine or a human.

"*Staphylococcus*" as used herein, refers to any and all bacterial species belonging to the genus *Staphylococcus*. This encompasses any and all Staphylococcal species including, but not limited to, *S. schleiferi, aureus, S. epidermidis S. pseudintermedius, S. hyicus, S. agnetis, S. lugdunensis* and *S. chromogenes*.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics. In certain embodiments, the condition is bacterial infection.

The term "therapeutic" as used herein means a treatment and/or prophylaxis. A therapeutic effect is obtained by suppression, remission, or eradication of a disease state.

As used herein, "topical administration" or "topical application" refers to a medication applied to body surfaces such as the skin or mucous membranes.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Description

The present invention relates to the unexpected discovery that fosmidomycin, an inhibitor of the non-mevalonate pathway for isoprenoid biosynthesis, can be used to treat a bacterial infection in a mammal, such as, but not necessarily limited to, a companion and/or an agricultural animal. Fosmidomycin can also be used to treat a bacterial infection in an avian species. In one embodiment, fosmidomycin is used to treat a *Staphylococcus* infection. In another embodiment, fosmidomycin is used to treat a drug-resistant *Staphylococcus* infection.

*Staphylococcus* and the Non-Mevalonate Pathway

The majority of studies looking at metabolism and biology of *Staphylococcus* have focused on *S. aureus*. While *S. aureus* is an important pathogen in humans and animals, there are many other *Staphylococcus* species of greater importance to veterinary medicine. Early biochemical experiments conducted primarily with *S. aureus*, led to the conclusion that *Staphylococcus* uses the mevalonate pathway to synthesize essential isoprenoids. Given that mammals use the same pathway, it has been assumed that targeting isoprenoid biosynthesis is not a viable strategy to treat bacterial infections in humans or other animals. Data disclosed herein in the present invention show that this essential metabolic pathway differs between *Staphylococcus* species associated with animals other than humans and non-human primates. These data point to inhibitors of the non-mevalonate pathway, such as fosmidomycin, as antimicrobials to treat certain *Staphylococcus* infections in animals, including those caused by multi-drug resistant strains. This discovery has important implications for human health, as *Staphylococcus* species typically associated with animal disease can occasionally cause infections in humans. For example, *S. schleiferi* and *S. pseudintetmedius* were first identified from human infections, and cause occasional, but serious, meningitis and sepsis in immune-compromised patients (Jindal et al. (2015) Pediatr Infect Dis J 34:329; Kuan et al. (2016) Int Forum Allergy Rhinol doi:10.1002/alr.21732).

The main target of fosmidomycin is the Dxr protein, but there is evidence that it can also inhibit a downstream enzyme, IspD, in vitro and in vivo (Zhang et al. (2011) Biochemistry 50:3570-3577). As is the case with any antibiotic, resistance to fosmidomycin could develop in *Staphylococcus*, either by blocking entry or accumulation of the drug in the bacterium, or via mutations in the Dxr binding site, both of which have been reported in other pathogens. Fosmidomycin is a promising drug to treat infections caused by *Staphylococcus* species that use the non-mevalonate pathway. Fosmidomycin is extremely well tolerated and exhibits low toxicity in mammals. *Plasmodium falciparum*, the cause of malaria, also synthesizes isoprenoids via the non-mevalonate pathway, and fosmidomycin was shown to be effective in killing the parasite in culture, and achieved cure rates of 85-100% in clinical trials when administered alone or in combination with clindamycin (Borrmann et al. (2004) J Infect Dis 190:1534-1540; Missinou et al. (2002) Lancet 360:1941-1942).

Most bacteria synthesize isoprenoids via the non-mevalonate pathway. However, across different bacterial Phyla, there are examples of species that use the mevalonate pathway, including *Streptococcus, Lactobacillus, Myxococcus*, and *Borrelia*. In addition, some *Pseudomonas* species, including *P. mevalonii*, are known to use hydroxymethylglutaryl—CoA reductase (the third enzyme of the mevalonate pathway) for degradative functions (Beach et al. (1989) *J Bacteriol* 171:2994-3001; Scher and Rodwell (1989) Biochim Biophys Acta 1003:321-326). Only *Listeria monocytogenes* and a few species of *Streptomyces* are known to possess both pathways, but in both organisms the non-mevalonate pathway plays the essential role in primary metabolism, while the mevalonate pathway is dispensable (Begley et al. (2008) Infect Immun 76:5392-540). Based on data from the present invention, *Staphylococcus* constitutes a unique example of a bacterial genus whose species utilize different isoprenoid biosynthesis pathways. Phylogenetic analyses shown herein (FIG. 3) are consistent with previous evolutionary studies that showed that the non-mevalonate pathway is the ancestral pathway in bacteria and the mevalonate pathway was acquired later through lateral gene transfer. This is further supported herein by the finding that deep-branching taxa (such as the *S. sciuri* and *S. intermedi* and *epidermidis* groups) use the mevalonate pathway.

An outstanding question is why *Staphylococcus* species evolved to use different pathways for isoprenoid synthesis. Without wishing to be bound by any specific theory, one possible explanation may lie in the secondary metabolites produced by these pathways: 1-hydroxy-2-methyl-2-(E)-butenyl 4-diphosphate (HMB-PP) is an intermediate of the non-mevalonate pathway and a potent activator of Vγ2/Vγ2 (also called Vγ9/Vγ2) T cells. HMB-PP is 1000 times more immune-stimulatory than IPP, the analogous intermediate produced by the mevalonate pathway. In humans, Vγ2Vγ2 cells make up 1-5% of peripheral T cells, but expand to >50% and rapidly traffic to barrier surfaces in response to pathogens that produce HMB-PP. Vγ2Vγ2 T cells are only found in humans and non-human primates. Without wishing to be bound by any specific theory, use of the mevalonate pathway by *S. aureus* and related species may provide a selective advantage and allow the pathogen to evade this aspect of the host immune response. These findings of divergent isoprenoid biosynthesis suggest one potential mechanism that *Staphylococcus* uses for host adaptation.

Methods of Treatment

The invention provides a method of treating or preventing a *Staphylococcus* infection in a mammal or in an avian species. In certain embodiments the method comprises administering to the mammal or avian species in need thereof a therapeutically effective amount of fosmidomycin, whereby the *Staphylococcus* infection is treated or prevented in the mammal or avian species.

Any type of mammal or avian species can be treated using the methods of the present invention. Types of mammals and avian species that can be treated include but are not limited to dogs, pigs, cows, horses, humans, cats, sheep, monkeys, apes, mice, bears, hamsters, birds, and gerbils. In certain embodiments, the mammal comprises a dog. In other embodiments, the mammal comprises a human.

In certain embodiments, fosmidomycin is administered to the mammal as a pharmaceutical composition further comprising at least one pharmaceutically acceptable carrier. Examples of pharmaceutically acceptable carriers include but are not limited to hydroxypropyl methylcellulose (HIPC) and polyethylene glycol 400 (PEG400).

In other embodiments, the subject is further administered at least one antibacterial agent. Antibacterial agents can include any agent that interferes with bacterial growth and reproduction. This includes agents that exhibit bactericidal or bacteriostatic properties. Non-limiting examples of antibacterial agents include but are not limited to clindamycin, amoxicillin, penicillin, erythromycin, tetracycline, meclocycline, sulfacetamide amoxicillin-clavulanic acid, ampicillin, cefazolin, chloramphenicol, ciprofloxacin, gentamicin, imipenem, oxacillin, rifampin, tetracycline, trimethoprim-sulfamethoxazole, and vancomycin. In one embodiment, the antibacterial agent comprises mupirocin. Mupirocin is also sold under trade names Bactroban or Centany. In certain embodiments, the fosmidomycin and the at least one antibacterial agent are co-administered to the mammal or avian species. In certain embodiments, the fosmidomycin and the at least one antibacterial agent are co-formulated. In other embodiments, the fosmidomycin is the only antibacterial agent administered to the mammal or avian species.

In some embodiments, the fosmidomycin is administered to the mammal or avian species by at least one administration route selected from the group consisting of topical, otic, inhalational, oral, rectal, vaginal, parenteral, transdermal, pulmonary, intranasal, buccal, ophthalmic, intrathecal, intracranial, and intravenous.

In certain embodiments, the *Staphylococcus* infection is caused by at least one *Staphylococcus* species selected from the group consisting of *S. schleiferi, S. pseudintermedius*, and *S. hyicus, S. chromogenes, S. sciuri*. In other embodiments, the *Staphylococcus* infection is caused by *S. schleiferi*. In yet other embodiments, the *Staphylococcus* infection is caused by an antibiotic resistant *Staphylococcus*. In other embodiments, the *Staphylococcus* infection can be caused by any species that uses the non-mevalonate pathway.

Formulations/Administration

The relative amounts of the active ingredient, the pharmaceutically acceptable carrier, and any additional ingredients in a pharmaceutical composition of the invention will vary, depending upon the identity, size, and condition of the subject treated. By way of example, the composition may comprise between about 0.005% and about 100% (w/w) of the active agent, or any fractions or multiples thereof. In one embodiment, 10 mg/ml of the active ingredient, fosmidomycin, is used for treatment.

Although the descriptions of pharmaceutical compositions provided herein are principally directed to pharmaceutical compositions that are suitable for ethical administration to mammals or avian species, it will be understood by the skilled artisan that such compositions are generally suitable for administration to humans and animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, commercially relevant mammals such as cattle, pigs, horses, and sheep, companion animals such as cats, birds, and dogs, agricultural species, and wildlife.

The regimen of administration may affect what constitutes an effective amount. The therapeutic formulations may be administered to the subject either prior to or after the onset of a condition considered herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a mammal or avian species, may be carried out using known procedures, at dosages and for periods of time effective to treat a condition considered herein in the mammal or avian species. An effective amount of the therapeutic compound necessary to achieve a therapeutic effect may vary according to factors such as the state of the disease or disorder in the subject; the age, sex, and weight of the subject; and the ability of the therapeutic compound to treat a condition considered herein in the subject. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and then gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a condition considered herein in a patient.

In certain embodiments, the compositions comprising a compound contemplated within the invention are formulated using one or more pharmaceutically acceptable excipients or carriers. In certain embodiments, the pharmaceutical compositions of the invention comprise a therapeutically effective amount of at least one compound contemplated within the invention and a pharmaceutically acceptable carrier. Pharmaceutically acceptable carriers, which are useful, include, but are not limited to, hydroxypropyl methylcellulose (HPC), polyethylene glycol 400 (PEG400), glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent which delays absorption, for example, aluminum monostearate or gelatin.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Formulations may be employed in admixtures with conventional excipients, i.e., pharmaceutically acceptable organic or inorganic carrier substances suitable for oral, otic, parenteral, nasal, intravenous, subcutaneous, enteral, or any other suitable mode of administration, known to the art. In certain embodiments, the administration comprises topical administration. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. An illustrative preservative is a combination of about 0.5% to 2.0% benzyl alcohol and 0.05% to 0.5% sorbic acid.

The composition may include an antioxidant and a chelating agent that inhibit the degradation of the compound. Selected antioxidants for some compounds are BHT, BHA, α-tocopherol and ascorbic acid in the exemplary range of about 0.01% to 0.3%, such as BHT in the range of 0.03% to 0.1% by weight by total weight of the composition. For example, the chelating agent is present in an amount of from 0.01% to 0.5% by weight by total weight of the composition. Illustrative chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are illustrative antioxidant and chelating agent respectively for some compounds, other suitable and equivalent antioxidants and chelating agents may be substituted as would be known to those skilled in the art.

Routes of administration of any of the compositions of the invention include nasal, inhalational, topical, oral, buccal, rectal, pleural, peritoneal, vaginal, intramuscular, subcutaneous, transdermal, epidural, intratracheal, otic, intraocular, intrathecal and intravenous. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Such formulations may be applied to the skin directly or through the use of swabs, applicators, spatulas and the like, as well as in the form of transdermal patches. In certain embodiments, the patch minimizes loss of pharmaceuticals through washing, friction, scratching and/or rubbing of the skin. In other embodiments, the patch increases absorption of the pharmaceutical through the skin, while minimizing the exposure of the skin to the pharmaceutical.

Topically administrable formulations may, for example, comprise from about 0.005% to about 10% (w/w) active ingredient, although the concentration of the active ingredient may be as high as the solubility limit of the active ingredient in the solvent. In certain embodiments, the active ingredient in the topical formulation comprises 10 mg/ml fosmidomycin. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, U.S. Pat. No. 6,323,219).

In alternative embodiments, the pharmaceutical composition of the invention may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition of the invention should be applied in an amount effective to affect desired changes. As used herein, "amount effective" shall mean an amount sufficient to cover the region of skin surface where a change is desired. An active compound should be present in the amount of from about 0.0001% to about 15% by weight volume of the composition; or in an amount from about 0.0005% to about 5% of the composition; or in an amount of from about 0.005% to about 1% of the composition. Such compounds may be synthetically-or naturally derived.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for topical administration, such as liniments, lotions, oil-in-water or water-in-oil emulsions such as creams, ointments or pastes, transdermal patches, and solutions or suspensions that are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention will depend on the age, sex and weight of the mammal or avian species, the current medical condition of the mammal or avian species and the progression of a condition considered herein in the mammal or avian species being treated. The skilled artisan will be able to determine appropriate dosages depending on these and other factors.

In certain embodiments, the compositions of the invention are administered to the mammal or avian species in dosages that range from one to five times per day or more. In other embodiments, the compositions of the invention are administered to the subject in range of dosages that include, but are not limited to, once every day, once every two days, once every three days, once a week, once every two weeks, once a month, or even less frequently, such as a one-time administration.

It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. Capsid assembly inhibitors exhibiting high therapeutic indices are a specific example. The data obtained from cell culture assays and animal studies is optionally used in formulating a range of dosage for use in human. The dosage of such capsid assembly inhibitors lies preferably within a range of circulating concentrations that include the $ED_{50}$ with minimal toxicity. The dosage optionally varies within this range depending upon the dosage form employed and the route of administration utilized.

Kits

In certain embodiments, the present invention is directed to a kit comprising a packaged pharmaceutical composition comprising a container holding a therapeutically effective amount of a compound of the invention, alone or in combination with a second pharmaceutical agent; and instructions for using the compound to treat, prevent, or reduce one or more symptoms of a condition considered herein in a patient.

In one embodiment, the kit comprises fosmidomycin and instructional material for use thereof in treating or preventing a bacterial infection in a mammal or avian species. In another embodiment, the kit comprises (i) fosmidomycin and (ii) an antibacterial agent and (iii) instructional material for use thereof in treating or preventing a bacterial infection in a mammal or avian species. In yet another embodiment, kit comprises fosmidomycin and instructional material for use thereof in treating or preventing a *Staphylococcus* infection in a mammal or avian species. In another embodiment, the kit comprises (i) fosmidomycin and (ii) an antimicrobial agent and (iii) instructional material for use thereof in treating or preventing a *Staphylococcus* infection in a mammal or avian species.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods

Bacterial Strains, Media, and Growth Conditions

*Staphylococcus* isolates were collected at the Matthew J. Ryan Veterinary Hospital of the University of Pennsylvania. *S. schleiferi* biochemical identification was carried out on a MicroScan Walkaway 40 PC20 Gram-positive combo-panel (Dade Behring, Sacramento, Calif.). Four banked *S. schleiferi* strains were selected for whole genome sequencing: 1360-13, 2142-05, 2317-03, and 5909-02. FIG. 5 contains a full list of *S. schleiferi* strains used in this study and their associated metadata. For biochemical assays, the following clinical isolates were used: *S. aureus* (MRSA; USA100, 3964), *S. aureus* (MSSA; 3899), *S. pseudintermedius* (MSSP; 5317), *S. pseudintermedius* (MRSP; 11680P), *S. sciuri* 1250OP-14, *S. epidermidis* 11510P-12, and *S. lugdunensis* F36680.

DNA Purification and Sequencing

*S. schleiferi* genomic DNA was purified, sequenced, and assembled into complete genomes as previously described (Misic et al., (2015) Genome Announc. September 10; 3(5)). Briefly, DNA was extracted from overnight cultures of *S. schleiferi* isolates using the Qiagen Genomic Tips Kit (Valencia, Calif., USA). DNA quantity and quality were assessed using a NanoDrop 1000 Spectrophotometer (Thermo Scientific, Pittsburgh, Pa., USA) and a Qubit Fluorometer (Life Technologies, Grand Island, N.Y., USA). Agarose gel electrophoresis was used to confirm high molecular weight DNA (>50 Kb) for SMRT sequencing on a Pacific Biosciences RSII platform. SMRTbell adapters were ligated and each strain of *S. schleiferi* was sequenced on one cell with one 120-minute movie. A hierarchical genome assembly process (HGAP) was performed for each strain using the HGAP.3 Module (Chin et al. (2013) Nat Methods 10:563-569). The genome was closed using manual refinement.

Comparative Genomics

For comparative genome analyses, sequences from Gen-Bank were retrieved for the following organisms: *S. schleiferi* 1360-13 (CP009470), *S. schleiferi* 2142-05 (CP0009762), *S. schleiferi* 5909-02 (CP009676, *S. schleiferi* 2317-03 (GenBank: CP010309), *S. pseudintermedius* HKU10-03 (N_014925.1), *S. pseudintermedius* ED99 (N_017568), *S. lugdunensis* HKU09-01 (CP001837), *S. lugdunensis* N920143 (FR870271.1), *S. epidermidis* ATCC 12228 (NC_004461), *S. epidermidis* RP62A (N_002976.3), *S. aureus* subspecies *aureus* ST398 (NC_017333), *S. aureus* subspecies *aureus* USA300 FPR3757 (NC_010079), *S. aureus* subspecies *aureus* COL (NC_006629), and *S. aureus* subspecies *aureus* NCTC 8325 (NC_007795). Sequences were downloaded from NCBI (ftp://ftp.ncbi.nlm.nih.gov). The circular, whole genomes were aligned using the BLAST Ring Image Generator (BRIG) v 0.95 (Alikhan et al. (2011) BMC Genomics 12:402) and the Basic Local Alignment Search Tool (BLAST v 2.2.22) (Camacho et al (2009) BMC Bioinformatics 10:421). Functional gene categories were determined with Rapid Annotation using Subsystem Technology (RAST) v 2.0 (Aziz et al. (2008) BMC Genomics 9:75) and FigFam v70. Subsystems with a standard deviation of zero among species were removed. The remaining differentially abundant subsystems were clustered by a Pearson correlation and the bacterial species were clustered by a Spearman correlation using the hclust function in R (v. 3.2.0) (R Development Core Team. (2010) R Foundation for Statistical Computing, Vienna, Austria) to reveal species-specific subsystem clusters. The cutree function in R was used to identify groups with similar subsystem abundance profiles.

Antibiotic Susceptibility Assays

The minimal inhibitory concentration (MIC) of various antimicrobials (amoxicillin-clavulanic acid, ampicillin, cefazolin, chloramphenicol, ciprofloxacin, clindamycin, erythromycin, gentamicin, imipenem, oxacillin, penicillin, rifampin, tetracycline, trimethoprim-sulfamethoxazole, and vancomycin) was determined via broth microdilution on a MicroScan Walkaway 40 PC20 Gram-positive combo-panel (Dade Behring, Sacramento, Calif.). Enrofloxacin and marbofloxacin susceptibilities were determined via Kirby-Bauer disk diffusion as these drugs were not available on the pre-configured commercial test panel. Fosmidomycin MIC assays were performed following clinical laboratory standards. Fosmidomycin (Sigma, St. Louis, USA) was filter-sterilized with a 0.2 mm filter (Pall Corporation, Ann Arbor, USA) and was serially 2-fold diluted in a concentration range of 40.96-0.25 mg/mL. Tubes containing 1 mL Mueller-Hinton broth (Sigma) were inoculated with $5 \times 10^5$ colony forming units/mL. 50 µL of the appropriate fosmidomycin concentration was added to each tube containing the starter culture, and was incubated at 37° C. overnight with shaking at 250 rpm for 18-20 hours. The MICS were determined by visual inspection. The minimum bactericidal concentration (MBC) was determined by plating 200 µL of the drug-treated cultures onto Mueller-Hinton agar plates (Remel, Lenexa, USA). The lowest concentration at which there was no growth after a 24-hour incubation at 37° C. was determined to be the MBC. For the plate-based fosmidomycin growth assay, overnight cultures of *Staphylococcus* species grown in Mueller-Hinton broth were sub-cultured to Mueller-Hinton agar plates containing 50 µg/mL fosmidomycin and were incubated for 24 hours at 37° C. All assays were performed and the results were interpreted using Clinical Laboratory Standards Institute guidelines (CLSI. (2013)

Approved Standard-Fourth Edition. Clinical and Laboratory Standards Institute, Wayne, Pa., USA).

Phylogenetic Tree Construction and Metabolic Pathway Comparisons

Gene sequences of sodA from twenty-nine staphylococcal species were downloaded from NCBI. The sodA gene has previously been shown to be a good representative of *Staphylococcus* phylogeny (Poyart et al. (2001) J Clin Microbiol 39:4296-4301). The web-based tool "Phylogeny.fr" (Dereeper et al. (2008) Nucleic *Macrococcus caseolyticus* was set as the outgroup. Sequences were aligned with MUSCLE v3.7 (Edgar (2004) Nucleic Acids Res 32:1792-1797), poorly aligned regions were removed using Gblocks v0.91b (Castresana (2000) Mol Biol Evol 17:540-552), and the phylogenetic tree was reconstructed using the maximum likelihood method implemented in PhyML v3.0 (Guindon et al. (2010) Syst Biol 59:307-321). Tree rendering was performed using TreeDyn v198.3 (Chevenet et al. (2006) BMC Bioinformatics 7:439) and bootstrap values are indicated on the branches. Metabolic pathway reconstructions of each strain were compared in silico using the "terpenoid backbone biosynthesis" pathway from KEGG (Kanehisa et al. (2014) Nucleic Acids Res 42:D199-205).

Example 1: High-Quality Genome Sequences for *S. schleiferi* Using Long-Read Sequencing Technology Complete genome sequences of four clinical isolates of *S. schleiferi*, a common commensal and a leading cause of skin and ear infections in dogs were previously reported (Misic et al., (2015) Genome Announc. September 10; 3(5)). Sequencing each strain using Pacific Biosciences (PacBio) Single Molecule, Real Time (SMRT) technology yielded between 45,000-87,000 reads per strain with an NS0 read length of approximately 6.5-10 kb (FIG. 6A). Reads of this length have been shown to greatly reduce de novo genome assembly complexity (Roberts et al. (2013) Genome Biol 14:405). Consistent with this notion, the sequences for each *S. schleiferi* strain assembled to form a single contig, representing the bacterial chromosome, with a depth of coverage ranging from 59-140X with >99.99% consensus accuracy (FIG. 6A). This depth of coverage for PacBio sequencing was recently predicted to resolve assembly gaps in most staphylococcal genomes (Koren et al. (2015) Curr Opin Microbiol 23:110-120). The long reads produced by this approach improved the ability to assemble highly repetitive regions of the *S. schleiferi* genome. For example, rRNA operons represent some of the longest repetitive regions in most bacterial genomes, and therefore pose the biggest challenge for assembly. In addition, clustered regularly interspaced short palindromic repeat (CRISPR) loci also pose a challenge to assembly as they are comprised of a variable number of short, repetitive sequence elements. SMRT sequencing generated numerous long reads that completely spanned both of these difficult-to-assemble regions of the bacterial genome, thereby providing unambiguous assembly (FIGS. 6B-6C). Taken together, these data show that high-quality finished genomes have been generated for this important veterinary pathogen.

Example 2: Comparative Genomic Analysis of Staphylococcal Species

To better understand the population genetics of veterinary *Staphylococcus* and identify putative drug targets, the *S. schleiferi* genomes were compared with published genome sequences from *Staphylococcus* species associated with human and veterinary hosts. Genomes from *S. schleiferi, S. pseudintermedius, S. epidermidis*, and *S. lugdunensis* were aligned to the *S. aureus* USA300 genome using BLAST v 2.2.22 and visualized and with BRIG v0.95. A visual inspection of the circular genome alignments revealed genomic regions that were present in the human-associated *Staphylococcus* strain USA300, but absent from veterinary-associated species (FIG. 1A, arrows). Similarly, other regions were absent from all species examined, except for *S. aureus* USA300 (FIG. 1A, arrowheads). To systematically compare these alignments, genomes were annotated with Rapid Annotation through Subsystems Technology (RAST) and differentially abundant subsystems were identified. From 382 total subsystems, 147 were conserved with an equal number of genes present in each subsystem across all genomes examined. In contrast, genes in 235 subsystems were differentially abundant between two or more species.

To identify relationships within the subsystems data, a hierarchical clustering was performed to group bacterial strains based on similar subsystems profiles (FIG. 1B, top dendrogram), as well as to group subsystems (FIG. 1B, rows) that were enriched in human-associated (*S. aureus, S. epidermidis*, and *S. lugdunensis*) or veterinary-associated (*S. schleiferi* and *S. pseudintermedius*) species. Strains that belonged to the same species clustered most closely together (FIG. 1B, top dendrogram). The human- and veterinary-associated *Staphylococcus* species segregated, indicating that they are predicted to differ in their functional gene content. At least three distinct subsystems clusters emerged from this analysis. Cluster 1 consisted of fifteen subsystems enriched in all four *S. aureus* strains, but absent from all other strains and species. This subsystem cluster included adhesins, pore-forming cytolysins, and genes involved in trehalose metabolism (FIG. 1D), consistent with previous studies of virulence factors in *S. aureus* (Powers et al. (2014) PLoS Pathog 10:e1003871; Lowy (1998) N Engl J Med 339:520-532; Schlievert (1993) J Infect Dis 167:997-1002). Cluster 2 also consisted of fifteen subsystems which were absent from veterinary and canine-associated *Staphylococcus*, but which were present across all other species examined (FIG. 1C). The mevalonate pathway for isoprenoid biosynthesis was found to be in cluster 2. Isoprenoids are an essential class of natural products and staphylococci have been shown to use the mevalonate pathway for isoprenoid biosynthesis (Odom (2011) PLoS Pathog 7:e1002323; Wilding et al. (2000) J Bacteriol 182:4319-4327). Further examination of the canine-associated *Staphylococcus* (cluster 3, thirteen subsystems) showed that these species used the non-mevalonate pathway, an alternative route to isoprenoid biosynthesis (FIG. 1E). Without wishing to be bound by any specific theory, these data suggest that human-associated and canine-associated staphylococcal species use different routes to generate an essential class of natural compounds.

Figures 2A, 2B:
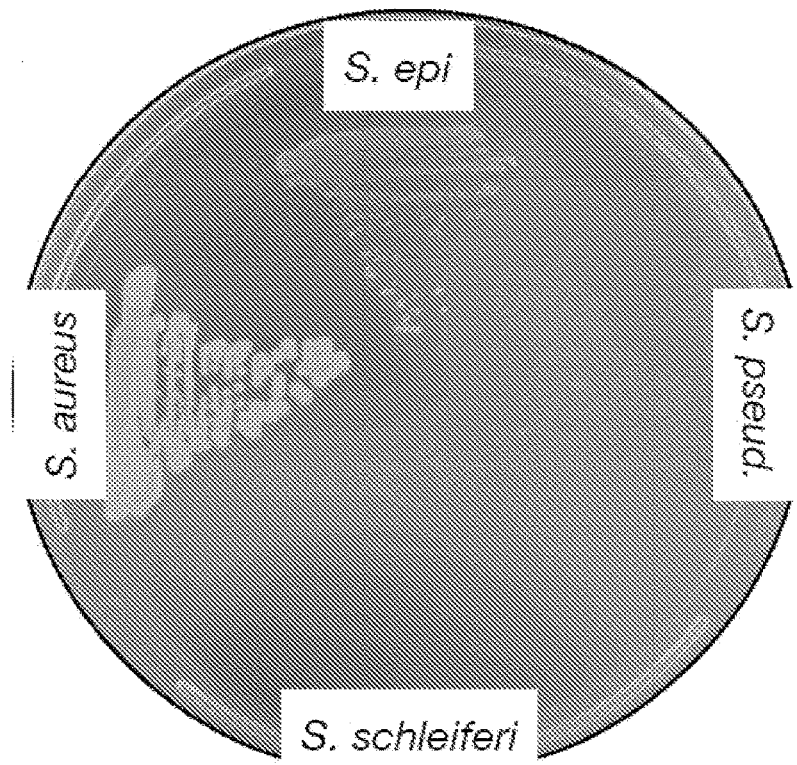
FIGS. 2A-2B illustrate the finding that fosmidomycin selectively kills *Staphylococcus* species associated with companion animal infections.

Example 3: Fosmidomycin Selectively Kills Bacteria Associated with Veterinary Skin and Ear Infections Isoprenoid biosynthesis is a highly conserved and essential process in bacteria, eukaryotes, and plants (Wilding et al. (2000) J Bacteriol 182:4319-4327; Lange et al. (2000) Proc Natl Acad Sci USA 97:13172-13177), and inhibitors have been used to target both the mevalonate and the non-mevalonate pathway. It was hypothesized that if *S. schleiferi* and *S. pseudintermedius* used the non-mevalonate pathway to synthesize isoprenoids, they should be sensitive to killing by the drug fosmidomycin, a phosphonic acid derivative that blocks the first committed step of the non-mevalonate pathway via inhibition of the 1-deoxy-D-xylulose 5-phosphate reductoisomerase (Dxr) (Steinbacher et al. (2003) J Biol Chem 278:18401-18407). To test this hypothesis, bacteria were grown on agar plates containing 50 µg/mL fosmidomycin. S. aureus and S. epidermidis, both of which are associated with human skin and are reported to use the mevalonate pathway (Lange et al. (2000) Proc Natl Acad Sci USA 97:13172-13177), grew in the presence of fosmidomycin. In contrast, fosmidomycin completely restricted growth of S. schleiferi and S. pseudintermedius (FIG. 2A). MIC and MBC assays were used to quantify fosmidomycin activity against a panel of Staphylococcus species. While S. aureus, S. lugdunensis and S. epidermidis grew normally even in the presence of 256 µg/ml of the drug, S. schleiferi, S. pseudintermedius, and S. sciuri were inhibited by fosmidomycin concentrations as low as 0.5 µg/mL, and killed by concentrations of 4-16 µg/mL (FIG. 2B). These results provided a biochemical validation of the comparative genomics data detailed herein (FIG. 1), and demonstrated that this antibiotic is active against specific Staphylococcus species, which primarily cause disease in animals. Fosmidomycin inhibited S. schleiferi strain 1360-13, which exhibits a multi-drug resistant phenotype (FIG. 5), demonstrating that the non-mevalonate pathway is a target to kill or inhibit drug resistant Staphylococcus species that are otherwise difficult to treat.

Figure 3:
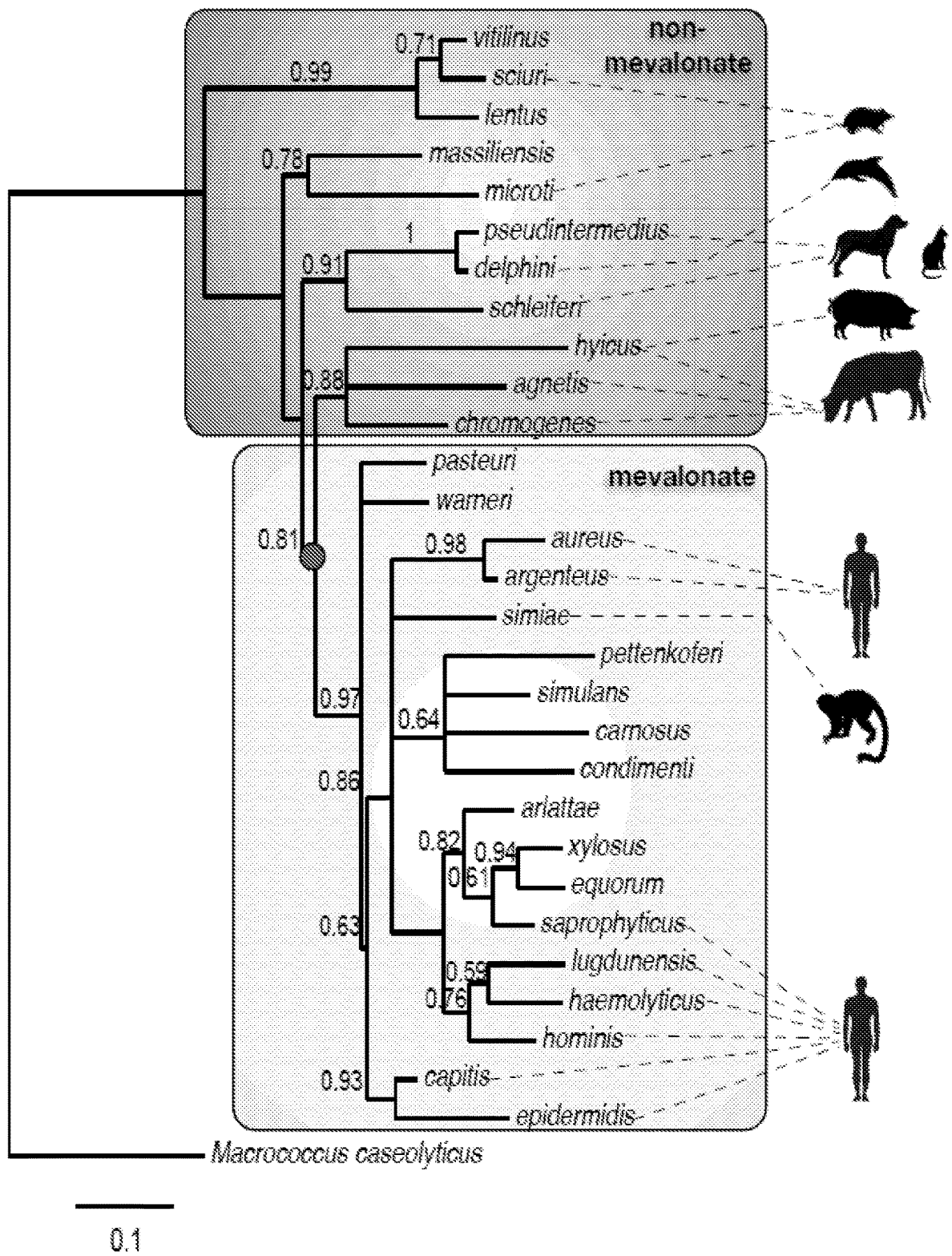
FIG. 3 is a dendrogram showing the evolution of isoprenoid biosynthesis in *Staphylococcus*. A maximum-likelihood phylogenetic tree was constructed from the superoxide dismutase (sodA) gene. Grey and white boxes indicate *Staphylococcus* species that utilize the non-mevalonate or mevalonate pathway, respectively. The silhouettes show host associations. The grey dot indicates the branch point in the tree where the mevalonate pathway use emerged. Bootstrap values are shown and the tree was rooted using *Macrococcus caseolyticus* as an outgroup.

Example 4: Divergent Isoprenoid Biosynthesis in the Genus Staphylococcus is Associated with Host Species Although many Gram-negative bacteria have been described to use the non-mevalonate pathway (Steinbacher et al. (2003) J Biol Chem 278:18401-18407; Heuston et al. (2012) Microbiology 158:1389-1401; Boucher and Doolittle (2000) Mol Microbiol 37:703-716), S. aureus and other Staphylococcus species have been used as an example of bacteria that use the mevalonate pathway (Odom (2011) PLoS Pathog 7:e1002323; Wilding et al. (2000) J Bacteriol 182:4319-4327). This prompted an expanded bioinformatics analysis beyond the 14 genomes highlighted in FIG. 1B to explore isoprenoid biosynthesis more broadly across the genus Staphylococcus. The superoxide dismutase (sodA) gene was used to construct a maximum-likelihood phylogenetic tree, and manual curation was used to determine which isoprenoid biosynthesis pathway was present (FIG. 3). This analysis showed that the non-mevalonate pathway was exclusively used by Staphylococcus species known primarily to cause disease in companion animals, agricultural species, and wildlife (FIG. 3, grey box). Use of the non-mevalonate pathway appears to be an ancestral trait, with use of the mevalonate pathway emerging later (FIG. 3, grey dot). Staphylococcus species that possess the mevalonate pathway formed a monophyletic group that included many notable human- and primate-associated species such as S. hominis, S. haemolyticus, S. simiae and S. aureus (FIG. 3, white box), Also included in this clade were S. equorum, S. gallinarum, and S. xylosus, which are often associated with horses, chickens, and mice, respectively.

Figures 4A, 4B:
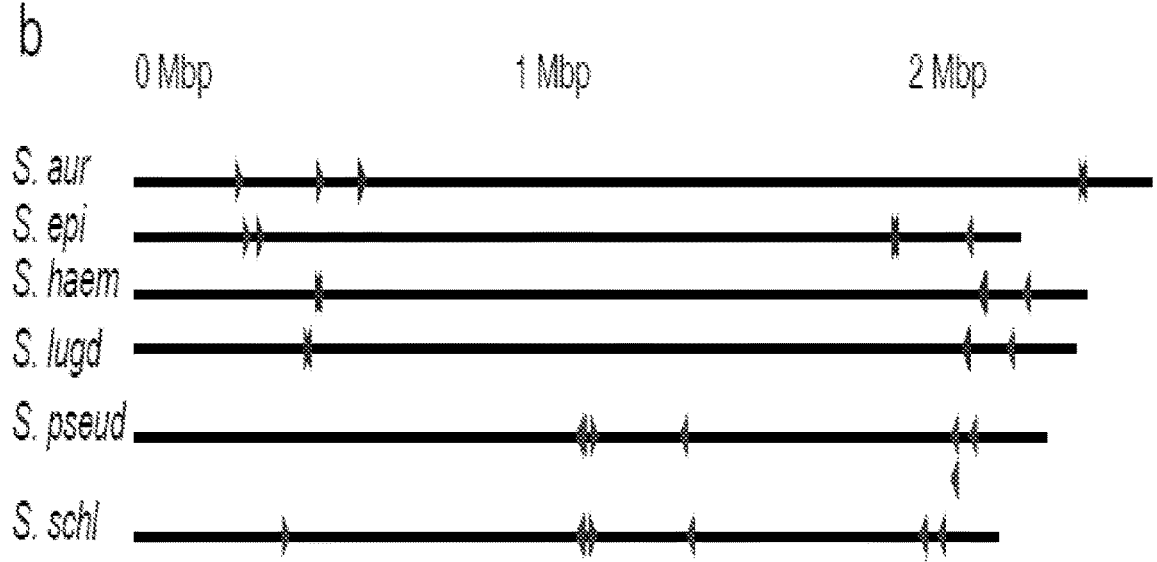
FIGS. 4A-4B are a series of graphs illustrating isoprenoid pathway organization in *Staphylococcus*.

Lateral gene transfer has been suggested to be common in the evolution of isoprenoid biosynthesis in bacteria (Boucher and Doolittle (2000) Mol Microbiol 37:703-716). Gene membership of both isoprenoid biosynthesis pathways in a range of Staphylococcus species was examined. Human-associated Staphylococcus species possessed every gene in the mevalonate pathway, but have also retained some non-mevalonate pathway enzymes including 2-methyl-D-erythritol 4-phosphate cytidylytransferase (IspD) and 4-diphosphocytidyl-2C-methyl-D-erythritol kinase (IspE) (FIG. 4A). In contrast, veterinary-associated Staphylococcus species possessed all members of the non-mevalonate pathway but completely lacked genes of the mevalonate pathway (FIG. 4A). Genomic location of functionally related genes can reflect their evolutionary history. Similar to the Staphylococcus mevalonate pathway (FIG. 4B and Wilding et al. (2000) J Bacteriol 182:4319-4327), the non-mevalonate pathway genes were not concentrated in one area of the genome, but were dispersed, and this argues against a recent lateral transfer event (FIG. 4B).

Example 5: Fosmidomycin Safety Trial for Otic Application in Dogs

Figures 7A, 7B, 7C:
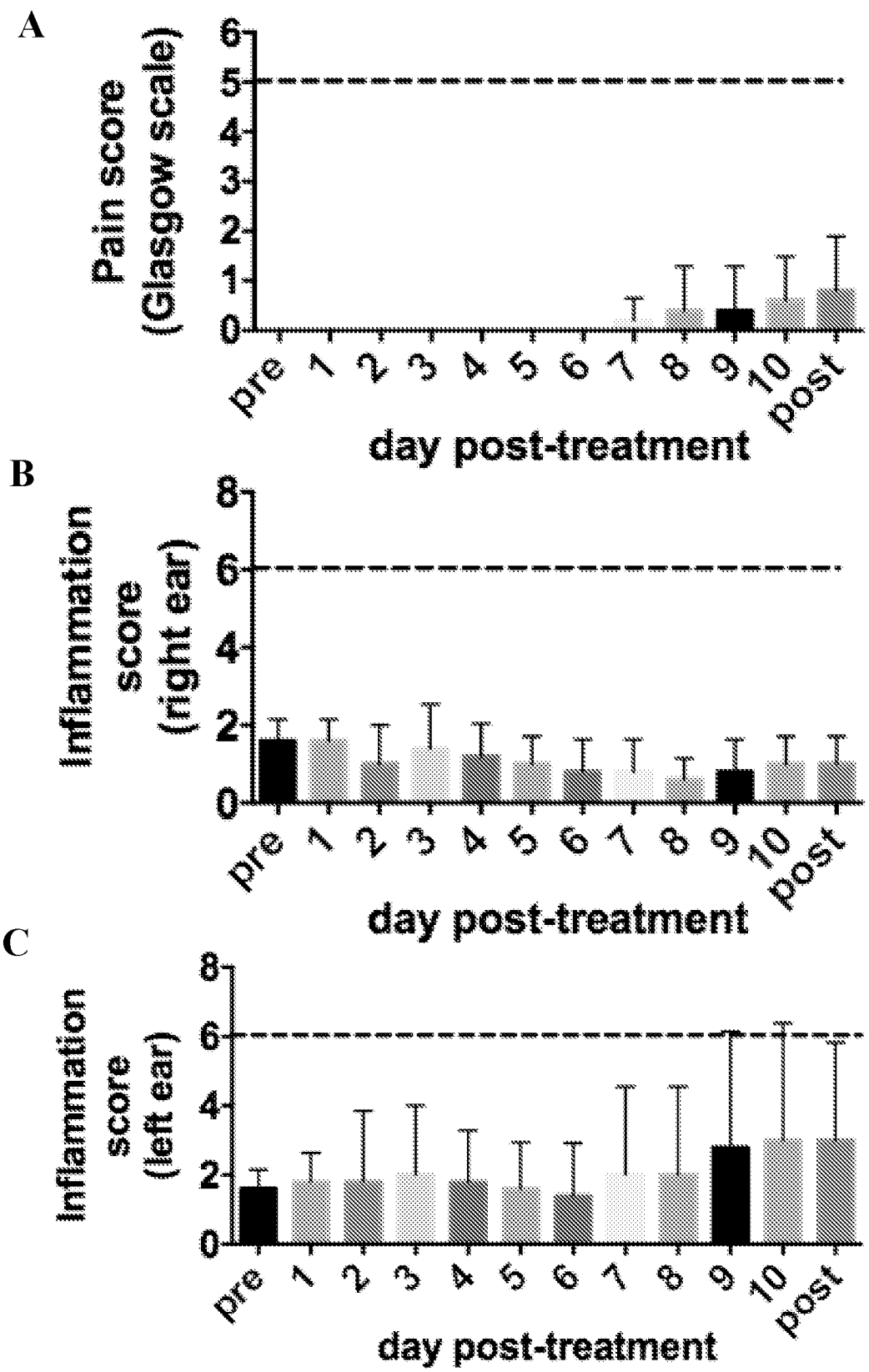
FIGS. 7A-7C are a series of plots illustrating the outcome of a fosmidomycin safety trial for otic application in dogs. Five colony dogs were used in the safety study. Four of the five dogs were homozygous for ectodermal dysplasia, while the remaining dog was a carrier (heterozygote). Each dog was treated with 100 micrograms of fosmidomycin resuspended in water and applied twice daily to both ears. Pain and inflammation were assessed using the Short Form of the Glasgow Composite Pain Scale (FIG. 7A) and the Otitis Index Score (FIG. 7B and FIG. 7C), respectively. Clinical scoring was carried out prior to fosmidomycin treatment ("pre"), each day of drug application for 10 days, and one day after the cessation of treatment ("post"). Bars represent the mean and standard deviation of scores for the group of 5 dogs at each timepoint. Dotted lines represent field-standard thresholds for clinically significant pain or inflammation.

Five research dogs were used in a safety study testing otic application of fosmidomycin. Four of the five dogs were homozygous for ectodermal dysplasia, while the remaining dog was a carrier (heterozygote). Dogs with ectodermal dysplasia can have a skin barrier defect, thus this provided a more sensitive canine model for detecting safety issues with compounds applied directly to the skin and ear. The study was carried out by treating each dog with 100 micrograms of fosmidomycin resuspended in sterile water and applied twice daily to both ears. Pain and inflammation were assessed using the Short Form of the Glasgow Composite Pain Scale (FIG. 7A) and the Otitis Index Score (FIG. 7B and FIG. 7C), respectively. Clinical scoring was carried out by a board-certified veterinary dermatologist prior to fosmidomycin treatment ("pre"), each day of drug application for 10 days, and one day after the cessation of treatment ("post"). Across the cohort of dogs in the study, pain and inflammation scores remained clinically insignificant, even in dogs with ectodermal dysplasia, demonstrating that fosmidomycin was safe to apply to the skin and ears.

Example 6: Optimization of Otic and Skin Formulation

While initial safety trials were conducted with fosmidomycin resuspended in sterile water, additional formulations were generated specifically for otic and skin applications. Proper formulation helps to stabilize the compound, prevent microbial growth during storage, and provides the proper consistency for skin and ear applications. Toward this end, two separate formulations were generated, and testing was carried out using standard microbiological assays to ensure activity (as determined by MIC measurements against Staphylococcus isolates derived from affected dogs).

Skin formulation: 10 mg/mL fosmidomycin in 1-2% hydroxypropyl methylcellulose (HPC). This formulation produced a viscosity of approximately 5,000 centipoise (for comparison, honey is 15,000 centipoise), resulting in a gel-like product that was amenable to spreading and was sufficiently occlusive, without being oily. The product was tested for activity in microbiological assays. The compound exhibited a MIC of <3 micrograms/milliliter against both Staphylococcus schleiferi and Staphylococcus pseudintermedius in liquid culture.

Otic formulation: 10 mg/mL fosmidomycin in 90-95% Polyethylene glycol 400 (PEG400). This formulation was ideal for otic applications for a number of reasons. First, PEG400 has inherent preservative properties, thereby improving shelf life. The formulation also produced a viscosity that prolonged contact and reduced elimination of the drops through run-out or head shaking. The product was tested for activity in microbiological assays. The compound exhibited a MIC of <4 micrograms/milliliter against both *Staphylococcus schleiferi* and *Staphylococcus pseudintermedius* in liquid culture.

Example 7: Use of Fosmidomycin for Treatment of *Staphylococcus* Infections in Agricultural Animals Data presented herein demonstrated the use of fosmidomycin as a safe and effective new therapy for the treatment of companion animal skin and ear infections caused by *Staphylococccus* species (particularly *S. schleiferi* and *S. pseudintermedius*). Data herein also support the treatment strategy as being effective against a range of *Staphylococcus* species that cause disease in agricultural animals. For example, data support the conclusion that fosmidomycin would be effective against both *S. hyicus* and *S. chromogenes*, two species that are known to produce potent exfoliative toxins, which damage the skin and lead to exudative epidermitis in suckling and recently weaned pigs. Moreover, *S. chromogenes* is one of the most common coagulase-negative *Staphylococcus* (CNS) species isolated from bovine mastitis cases. Although CNS mastitis is often subclinical, studies from other groups have shown that it can result reduced milk production. Fosmidomycin could be used to treat CNS mastitis and would complement current therapies that target mastitis caused b*S. aureus*.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a *Staphylococcus* infection in a mammal or avian species, wherein the *Staphylococcus* infection is caused by a species of *Staphylococcus* that utilizes the non-mevalonate pathway for isoprenoid biosynthesis, wherein the species of *Staphylococcus* that utilizes the non-mevalonate pathway for isoprenoid biosynthesis is not *Staphylococcus hyicus*; the method comprising administering to the mammal or avian species in need thereof a therapeutically effective amount of fosmidomycin, or a salt, solvate, tautomer, enantiomer or diastereomer thereof, whereby the *Staphylococcus* infection is treated in the mammal or avian species.

2. The method of claim 1, wherein the *Staphylococcus* infection is caused by at least one *Staphylococcus* species selected from the group consisting of *S. schleiferi, S. pseudintermedius, S. sciuri, S. hyicus*, and *S. chromogenes*.

3. The method of claim 1, wherein the *Staphylococcus* infection is caused by an antibiotic resistant *Staphylococcus*.

4. The method of claim 1, wherein the mammal or avian species is selected from the group consisting of a dog, pig, cow, horse, bird, and human.

5. The method of claim 1, wherein the mammal comprises a dog.

6. The method of claim 1, wherein fosmidomycin is administered to the mammal or avian species as a pharmaceutical composition further comprising at least one pharmaceutically acceptable carrier.

7. The method of claim 1, wherein the mammal or avian species is further administered at least one antibacterial agent.

8. The method of claim 7, wherein the fosmidomycin and the at least one antibacterial agent are co-administered to the mammal or avian species.

9. The method of claim 7, wherein the fosmidomycin and the at least one antibacterial agent are co-formulated.

10. The method of claim 1, wherein the fosmidomycin is administered to the animal by at least one administration route selected from the group consisting of otic, topical, inhalational, oral, rectal, vaginal, parenteral, intranasal, buccal, ophthalmic, intrathecal, intracranial, and intravenous.

11. The method of claim 1, wherein the fosmidomycin is the only antibacterial agent administered to the mammal or avian species.

12. A method of treating a *Staphylococcus schleiferi* infection in a mammal or avian species, the method comprising administering to the mammal or avian species in need thereof a therapeutically effective amount of fosmidomycin, or a salt, solvate, tautomer, enantiomer or diastereomer thereof, whereby the *Staphylococcus schleiferi* infection is treated in the mammal or avian species.

13. The method of claim 12, wherein the *S. schleiferi* infection is caused by an antibiotic resistant *Staphylococcus*.

14. The method of claim 12, wherein the mammal or avian species is selected from the group consisting of a dog, pig, cow, horse, bird, and human.

15. The method of claim 12, wherein the mammal comprises a dog.

16. The method of claim 12, wherein fosmidomycin is administered to the mammal or avian species as a pharmaceutical composition further comprising at least one pharmaceutically acceptable carrier.

17. The method of claim 12, wherein the mammal or avian species is further administered at least one antibacterial agent.

18. The method of claim 17, wherein the fosmidomycin and the at least one antibacterial agent are co-administered to the mammal or avian species.

19. The method of claim 17, wherein the fosmidomycin and the at least one antibacterial agent are co-formulated.

20. The method of claim 12, wherein the fosmidomycin is administered to the animal by at least one administration route selected from the group consisting of otic, topical, inhalational, oral, rectal, vaginal, parenteral, intranasal, buccal, ophthalmic, intrathecal, intracranial, and intravenous.

21. The method of claim 12, wherein the fosmidomycin is the only antibacterial agent administered to the mammal or avian species.

* * * * *